US009739720B2

(12) United States Patent
De Wel et al.

(10) Patent No.: US 9,739,720 B2
(45) Date of Patent: Aug. 22, 2017

(54) METHOD, COMPUTER SYSTEM AND APPARATUS FOR RECIPE GENERATION FOR AUTOMATED INSPECTION OF SEMICONDUCTOR DEVICES

(71) Applicant: KLA-Tencor Corporation, Milpitas, CA (US)

(72) Inventors: Koen De Wel, Oud-Heverlee (BE); Cedric Carette, Balen-Olmen (BE)

(73) Assignee: KLA-Tencor Corporation, Milpitas, CA (US)

( * ) Notice: Subject to any disclaimer, the term of this patent is extended or adjusted under 35 U.S.C. 154(b) by 153 days.

(21) Appl. No.: 13/885,136

(22) PCT Filed: Mar. 13, 2013

(86) PCT No.: PCT/IB2013/051964
§ 371 (c)(1),
(2) Date: Aug. 23, 2013

(87) PCT Pub. No.: WO2013/140302
PCT Pub. Date: Sep. 26, 2013

(65) Prior Publication Data
US 2015/0006103 A1    Jan. 1, 2015

Related U.S. Application Data

(60) Provisional application No. 61/612,507, filed on Mar. 19, 2012.

(51) Int. Cl.
*G01N 21/95* (2006.01)
*G01N 21/956* (2006.01)
(Continued)

(52) U.S. Cl.
CPC ....... *G01N 21/9501* (2013.01); *G01N 21/956* (2013.01); *G03F 7/7065* (2013.01);
(Continued)

(58) Field of Classification Search
CPC ............ G01N 21/9501; G01N 21/956; G01N 2201/068; G05B 23/0229; G05B 23/0216;
(Continued)

(56) References Cited

U.S. PATENT DOCUMENTS 6,959,251 B2   10/2005   Coldren et al.
7,034,298 B2   4/2006    Miyai et al.
(Continued)

FOREIGN PATENT DOCUMENTS

CN        1645590        7/2005
JP       2004117130 A    4/2004
(Continued)

*Primary Examiner* — Mohamed Charioui
*Assistant Examiner* — Jeremy Delozier
(74) *Attorney, Agent, or Firm* — Simpson & Simpson, PLLC

(57) ABSTRACT

A method, a computer system and an apparatus are disclosed for inspection recipe generation for the automated inspection of semiconductor devices. In order to generate the inspection recipe a reference data set is used. Automatic inspection is carried out with an initial recipe on images of dies of the reference data set (reference wafermap). The detected inspection results from the automatic inspection are classified and the classified inspection results are compared with an expert classification of defects in dies. Overkill and underkill numbers are automatically generated. According to the overkill and underkill numbers the inspection recipe parameters are modified. Automatic inspection is repeated if the detection and/or the classification are below a predefined threshold.

25 Claims, 7 Drawing Sheets

(51) Int. Cl.
*G03F 7/20* (2006.01)
*H01L 21/66* (2006.01)
*G05B 23/02* (2006.01)

(52) U.S. Cl.
CPC ..... *G05B 23/0216* (2013.01); *G05B 23/0229* (2013.01); *H01L 22/12* (2013.01); *H01L 22/20* (2013.01); *G01N 2201/068* (2013.01); *G05B 2219/37224* (2013.01)

(58) Field of Classification Search
CPC .......... G05B 2219/37224; H01L 22/20; H01L 22/12; G03F 7/7065
See application file for complete search history.

(56) References Cited

U.S. PATENT DOCUMENTS

| | | |
|---|---|---|
| 2004/0188609 A1 | 9/2004 | Miyai et al. |
| 2005/0043903 A1 | 2/2005 | Nara et al. |
| 2005/0075841 A1 | 4/2005 | Peles et al. |
| 2005/0119844 A1 | 6/2005 | Lee et al. |
| 2006/0265145 A1* | 11/2006 | Huet ................. G01R 31/2846 702/35 |
| 2007/0047800 A1 | 3/2007 | Hiroi et al. |
| 2007/0053581 A1 | 3/2007 | Ueno et al. |
| 2008/0162065 A1 | 7/2008 | Takeda et al. |
| 2009/0088997 A1 | 4/2009 | Kikuchi et al. |
| 2009/0228217 A1 | 9/2009 | Fukushima |
| 2009/0290782 A1 | 11/2009 | Regensburger |
| 2010/0194422 A1* | 8/2010 | Ito ...................... G01R 31/3016 324/762.01 |

FOREIGN PATENT DOCUMENTS

| | | |
|---|---|---|
| JP | 2007071678 A | 3/2007 |
| JP | 2011-017609 | 1/2011 |
| KR | 20010037026 A | 5/2001 |
| WO | 2006/039584 | 4/2006 |
| WO | WO 2009/148876 | 12/2009 |

* cited by examiner

METHOD, COMPUTER SYSTEM AND APPARATUS FOR RECIPE GENERATION FOR AUTOMATED INSPECTION OF SEMICONDUCTOR DEVICES

CROSS REFERENCE TO RELATED APPLICATIONS

The present application is the U.S. national stage application pursuant to 35 U.S.C. §371 of International Application No. PCT/IB2013/051964, filed Mar. 13, 2013, which application claims benefit of U.S. Provisional Patent Application 61/612,507 filed Mar. 19, 2012, which applications are incorporated herein by reference.

FIELD OF THE INVENTION

The present invention relates to a method for recipe generation for automated inspection of semiconductor devices.

The present invention also relates to computer system for inspection.

The present invention also relates to an apparatus for inspection

BACKGROUND OF THE INVENTION

The Korean patent application KR 20010037026A discloses a method for establishing a recipe parameter in a wafer inspection process. The method is used to shorten the time taken to establish a recipe parameter and to reduce precision variation caused by the experience of an operator, therefore the recipe parameter of an inspection apparatus is stored in a library so that the recipe parameter is used in inspecting the wafer experiencing the same process. Optical or electrical recipe parameters vary according to the characteristic of the wafer to be inspected. The parameters are stored in a library. The characteristic of the wafer in inspection is inputted. Recipe parameters corresponding to the inputted characteristic of the wafer in inspection are read out from the library and automatically established.

The patent U.S. Pat. No. 6,959,251 B2 describes techniques for efficiently setting up inspection, metrology, and review systems for operating upon semiconductor wafers. Specifically, this involves setting up recipes that allows each system to accurately inspect semiconductor wafers. Pertinent information is gathered from these tools and presents the information to users in a way that reduces the time required to complete a recipe.

The international patent application WO 2009/148876 A1 describes a method and a system for generating information to be used for selecting values for parameter(s) of a detection algorithm. Without user intervention, a scan is performed of an area of a wafer using an inspection system. The method also includes selecting a portion of the defects from results of the scan based on a predetermined maximum number of total defects to be used for selecting values for the parameter(s) of the detection algorithm. The method further includes storing information, which can be used to select the values for the parameter(s) of the detection algorithm to be used for the inspection recipe without performing an additional scan of the wafer subsequent to the scan.

A method and a system for establishing a wafer testing recipe are disclosed in US 2009/290782 A1. A camera acquires images of a number of dice from a produced wafer. A software uses at least part of the images and composes a reference-image to be used as testing reference of a typical die image. Based on the reference-image single and/or repeatable elements of a die pattern are defined as a "zone of interest". A Detection-Policy is determined for each of the zone of interest or for a group of similar zones of interest and determining the algorithm that will be used by each of the Detection-Policy. The parameters of each of the Detection-Policy's algorithms are determined. The Reporting-policy is determined by defining a set of specific names of defect classes that could be used during inspection of a specific lot of wafers. A creating a "wafer testing recipe" is created by integrating the testing reference of a typical die image, the defined zones of interest, the determined Detection-Policies, the parameters of the determined Detection-Policies' algorithms, the determined Reporting-Policies and the determined Inspection-Policies.

According to prior art a method or system the initial recipe is executed on one wafer. The user takes the results offline and judges the performance of the recipe by reviewing individual die images/results. Some good dies are rejected, which is overkill, and some bad dies are accepted, which is underkill. Purpose of the tuning is to minimize both overkill and underkill. The user modifies one or more parameters of the inspection recipe to his/her best knowledge and saves the new version of the recipe and re-inspects the entire wafer. The newly generated results are reviewed again one by one and the recipe is modified again if results are not yet satisfactory. This sequence is repeated multiple times until the overkill/underkill result is within specifications.

There are multiple drawbacks with the old method is that each tuning iteration takes a long time, the complete wafer has to be re-inspected, and the results have to be reviewed on individual die/defect level. The recipe changes have to be saved in another version of the recipe. The user is responsible for this recipe management.

Additionally, there is no good feedback on inspection results. The user has to keep track of dies of interest for review, because the recipe development is a manual action and result review will be limited to a set of dies that is manageable by the user. There is no reference available and the user has to keep track of the expected results for the dies of interest. Tuning can only be done on dies of 1 wafer at a time. Typically one wants to tune on dies of multiple wafers/lots. Improvements in the recipe for one wafer do not necessarily mean this is a recipe improvement for other wafers as well.

A lot of iterations are needed in order to come to a tuned recipe, because of the limited feedback and it is not easy to judge the impact of recipe changes. This makes that the number of iterations is large, adding to the time of coming to a good recipe.

BRIEF SUMMARY OF THE INVENTION

It is an object of the invention to provide a method for recipe generation for automated inspection of semiconductor devices wherein recipe generation takes less time and provides feedback on the inspection result gained with the recipe.

The object is achieved by a method for inspection recipe generation for automated inspection of semiconductor devices, comprising the following steps:
using a reference data set for inspection recipe generation;
running automatic inspection with an initial recipe on images of dies of the reference data set;

classifying the detected inspection results from the automatic inspection and comparing the classified inspection results with an expert classification of defects in dies;

automatically generating overkill and underkill numbers; and modifying inspection recipe parameters and repeating the automatic inspection if the detection and/or the classification is below a predefined threshold.

It is a further object of the invention to provide a computer system for recipe generation for automated inspection of semiconductor devices wherein recipe generation takes less time and provides feedback on the inspection result gained with the recipe.

The object is achieved by a computer system for inspection recipe generation for automated inspection of semiconductor devices, wherein the computer system comprises:

a computer for using a reference data set for inspection recipe generation and running an automatic inspection with an initial recipe on images of dies of the reference data set;

a dialog, with a first window showing at least the reference data, a second window showing at least test data; a third window showing a tune map and a fourth window showing a classification table which enables a comparison between the classified inspection results and an expert classification of defects in dies, with regard to the overkill and underkill numbers;

an automatic generation and display of overkill and underkill numbers; and a modification of inspection recipe parameters and a repetition of the automatic inspection if the detection and/or the classification is below a predefined threshold.

A further object of the invention is to provide an apparatus for recipe generation for automated inspection of semiconductor devices wherein recipe generation takes less time, provides feedback on the inspection result gained with the recipe and obtains reliable and less time consuming inspection results.

The above object is achieved by an apparatus for inspection recipe generation for automated inspection of semiconductor devices comprising:

an inspection system, with at least an incident light illumination system; a camera arranged to receive light from a surface of the semiconductor device, wherein the light is converted to electric image data for further analysis;

a computer for using a reference data set for inspection recipe generation and running an automatic inspection with an initial recipe on images of dies of the reference data set; and a least one display, which is subdivided into a first window, a second window, a third window and a fourth window; wherein the first window showing at least the reference data, the second window showing at least test data; the third window showing a tune map and the fourth window showing a classification table which enables a comparison between the classified inspection results and an expert classification of defects the images, with regard to the overkill and underkill numbers which are automatically generated and displayed.

The inventive method for inspection recipe generation for automated inspection of semiconductor devices does not necessarily need an inspection system for the generation of a tune map. A user can work offline using and load a previously stored reference data set for inspection recipe generation. The reference data are configured as a tune map or a reference map. Prior to the upload of the tune map or the reference map to the computer a refining, tuning and modifying of the existing reference map or the existing tune map is carried. Additionally, an existing inspection recipe is stored and is uploaded to a computer. Prior to the upload of the existing inspection recipe to the computer a refining, tuning and modifying of the existing initial inspection recipe is carried out. The method can run on inspection recipes stored in a memory and the inspection parameters can be tested and/or tuned in order to tailor the inspection recipe.

The tune map contains dies of interest and a die classification is selectable by the user. Dies from different semiconductor devices are added to the tune map. A classification table shows comparison results between the reference data set (tune map or the reference map) and a test data set, wherein the test data set is a result of an inspection using an inspection recipe.

In many cases the inventive method is implemented on an inspection system, which has a computer and a dialog (display). Via the dialog the user or process engineer can influence and monitor the generation of the inspection recipe for automated inspection of semiconductor devices. In this case the user does not work offline. The user can re-inspect the semiconductor device (wafer) on a chuck, with the recipe settings in memory. The results are cleared when res-inspecting again. The reference wafermap is displayed in the dialog. It is typically an output wafermap of a previous inspection that is used to specify the dies to be re-inspected.

Prior to using a reference data set (tune map or the reference map) for inspection recipe generation, the generation of the data set and of an initial recipe is carried out. In case no wafer is on the chuck, a semiconductor device (wafer) is loaded into the inspection system and a setup and a tune alignment is carried out. Then an automatic inspection of the loaded semiconductor device is carried out. The results are reviewed on die level. Dies are classified and die images are added together with all defect information to the tune map. The classification is done automatically by the system and may be overruled by the user where needed (=expert classification). A new semiconductor device is loaded into the inspection system if a knowledge database of dies of the tune map is not large enough. The automatic inspection of the newly loaded semiconductor device is carried out, accordingly.

The reference wafermap and the test wafermap are available in the same dialog. In other words the reference wafermap and the test wafermap are shown side by side on the display (user interface). The reference wafermap and the test wafermap are linked so that when selecting in one of the wafermaps a die or a classification the corresponding die in the other wafermap is selected as well.

Typically, the user of the test dialog does not want to re-inspect the whole wafer, but only certain dies or certain classes of dies. One possibility is to re-inspect a single die. Here the last inspection result is used as the reference wafermap. The users can simply review results by clicking on the dies in the reference wafermap and the selected die will be re-inspected after the user initiates the run in the inspection process. All dies that that have not been inspected will get the status "to be inspected" in the test wafermap. A further possibility is to re-inspect a class of dies. The dies are highlighted in the reference wafermap by clicking the name of the respective class in the classification table shown on the display. The selection can be undone by clicking on the class again. A regular re-inspection is carried out, if no die is selected in the reference wafermap or no class of dies is highlighted in the reference wafermap.

The inventive method can be used for setup, tune or optimize inspection recipes for automated inspection of semiconductor devices. Preferably, a semiconductor device is a patterned wafer (including LED or MEMS).

One possible embodiment of the invention is that semiconductor device (wafer) is loaded in an inspection system in order to create an initial inspection recipe. With the inspection system a tuning of the wafer alignment, a tuning of the die alignment and a creating of an optimal image set for a reference image is carried out. Once the setup is finalized the automatic inspection of the wafer starts, wherein the inspection recipe is used. The images (bitmap) captured during inspection are saved in an appropriate storage device. The images contain the dies on the wafer. During the inspection process at least one die is imaged and usually all dies on the surface of the wafer.

The inspection images are reviewed on die level and the dies are classified by expert according to the defect types (e.g. scratch, particle, epi defect, etc. . . . ). A tune map is generated, wherein a tune map comprises inspection images dies or samples and correct or ground truth defect classification per die. Not all dies of the inspected wafer need to be added to the tune map. A user adds only those dies which are representative. The tune map is a kind of knowledge database with examples for pass (correct dies) and all defect classes of interest. A tune map may comprise multiple defect classes or alternatively multiple tune maps may be used where each comprises only one defect class. The tune map or the reference map is a reference data set which is loaded to the inspection system. Offline inspection is carried out using the inspection recipe of one or several die of the tune map/reference map.

The offline inspection needs not necessarily be carried out on the computer of the inspection system. A user or process engineer can load the tune map/reference map to a remote computer and carry out the inspection recipe generation.

The inspection results are analyzed and interpreted. Overkill and underkill numbers are automatically generated. If the inspection results are "good enough" and the tune map/the knowledge database are large enough, which means that all pass and defect types are covered, the process for the inspection recipe generation comes to an end. In case the inspection results are not "good enough" the parameters (e.g. thresholds, feature sizes, etc.) of the inspection recipe are modified. It is as well possible that the modification of the recipe parameters is done automatically.

If the tune map/the knowledge database are not large enough, which means that not all pass and defect types are covered, a new wafer is loaded to the inspection system. With the new wafer the whole process of automatic inspection, review of the inspection results, adding dies to the tune map, loading tune map, analyzing/interpreting inspection results and the automatic generation of overkill and underkill is carried out again. The process for the inspection recipe generation comes to an end if the inspection results are "good enough" and the tune map/the knowledge database are large enough.

The main benefit of the invention is that recipes can be tuned (or optimized) OFFLINE (=without the need of an inspection tool). The tuning of recipes is based on stored recipes and stored wafermaps. The concept of the TUNE MAP helps to setup a database of 'perfectly classified dies' which serve as a 'perfect reference' when tuning a recipe for underkill/overkill. Several data sets can be loaded as a 'reference map' (with saved images). It is possible to build a reference wafermap with data from multiple wafers. The data set needed for the generation of a reference wafermap can be loaded from one or multiple tune map(s). There is no need to first inspect a wafer or a semiconductor device in order to generate inspection results. Another possibility is to use a result wafermap from an inspection on an inspection system or from an inspection in the tune environment. It is also possible that no reference map is used and in that case a real inspection will be carried out on the inspection system without making use of saved images. From the captured images the recipe is created and tuned.

The tune pane is used for the entire tuning process for obtaining a recipe. The inspection and classification parameters can be reached via shortcuts shown on the tune pane. Moreover, the inspection and classification parameters can be edited without the need to save the recipe before run in the tune pane.

It is required that a loaded reference wafermap is re-inspected. The inspection process will just execute the inspection recipe in memory. The reference wafermap is taken from the last run because the user would like to re-inspect images of a previously inspected wafer. In case the user woks offline, the possibility is offered to load a new reference wafermap. After loading the new reference wafermap successfully, the reference wafermap can be reviewed and the user can decide about the dies to be re-inspected It is as well possible to use a library of reference wafermaps. Reference wafermaps are typically maps with respective results for a certain inspection recipe. The recipe itself is validated on a set of die images. The user selects certain die images on which he wants to validate the inspection recipe. These images are collected over time and do not necessarily come from one single wafer. The amount of images on which the user wants to qualify the inspection recipe can vary from a few to several hundreds. A tune map (knowledge base) is created which can extend over time.

The invention is implemented in an apparatus for inspection recipe generation for automated inspection of semiconductor devices. The apparatus has an inspection system, with at least an incident light illumination system. Depending on the required application at least one dark-field illumination system is implemented as well. A camera is arranged to receive light from a surface of the semiconductor device (wafer) and the light is converted to electric image data for further analysis. A computer of the inspection system uses a reference data set for inspection recipe generation and running an automatic inspection. The automatic inspection can run with an initial recipe on images of dies of the reference data set. The man machine interface is realized with at least one display or dialog. The display is subdivided into a first window, a second window, a third window and a fourth window. The first window shows at least the reference data ("reference wafermap", "reference wafermap—result image", "reference wafermap—wafer surface defect list" and "reference wafermap—wafer die list"). The second window shows at least test data ("test wafermap", "test wafermap—result image", "test wafermap—wafer surface defect list" and "test wafermap—wafer die list"). The third window shows a tune map with a possibility to select and arrange dies. The fourth window shows a classification table which enables a comparison between images of the classified inspection results and images of an expert classification of defects. This is done, with regard to the overkill and underkill numbers which are automatically generated and displayed. An input device enables a modification of the inspection recipe parameters and repeating the automatic inspection if the detection and/or the classification is below a predefined threshold. The reference data set is a stored reference map or a tune map which is uploaded to the computer. A refining, tuning and modifying of the reference map or the tune map is carried out prior to the upload to the computer. The existing inspection recipe is stored and is uploaded to the computer. A refining, tuning and modifying of the existing initial inspection recipe is carried out prior to the upload to the computer.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
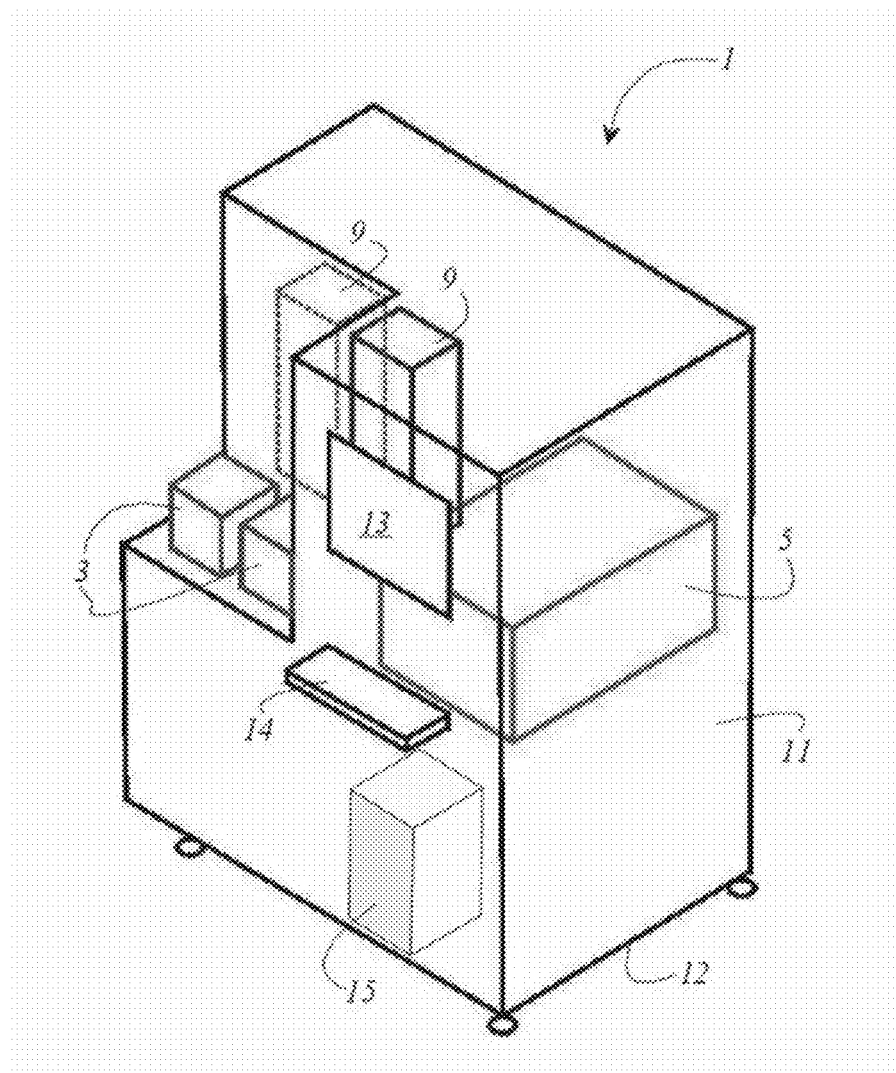
FIG. 1 shows a schematic representation of an inspection system for the inspection of semiconductor devices, respectively, wafers or disc-shaped objects.

Same reference numerals refer to same elements throughout the various figures. Furthermore, only reference numerals necessary for the description of the respective figure are shown in the figures. The shown embodiments represent only examples of how the invention can be carried out. This should not be regarded as limiting the invention.

The schematic representation of FIG. 1 shows an inspection system 1 for the inspection of semiconductor devices 100, wafers or disc-shaped objects respectively. According to this embodiment, the inspection system 1 of this embodiment has at least one cartridge element 3 for the semiconductor devices 100 (wafers). In an inspection unit 5 the images or image data, respectively, of the individual semiconductor devices 100 are recorded. At least one transport device 9 is provided between the at least one cartridge element 3 for the semiconductor devices 100 and the inspection unit 5. The system 1 is enclosed by a housing 11. Furthermore a computer system 15 is integrated into the inspection system 1, which receives the images or image data from the individual wafers measured and processes them. Additionally, the computer system 15 can be used to design a recipe for the inspection of the semiconductor devices 100. The inspection system 1 is provided with an interface 13 (display, dialog) and a keyboard 14. By means of an input device 14 (keyboard, mouse or the like) the user can perform data input for the control of the inspection system 1 or the input of parameters for improving the recipe creation, which is used for the inspection semiconductor devices in order to minimize under- and/or overkill. On the interface 13 the user can get information and feed back about the recipe design.

Figure 2:
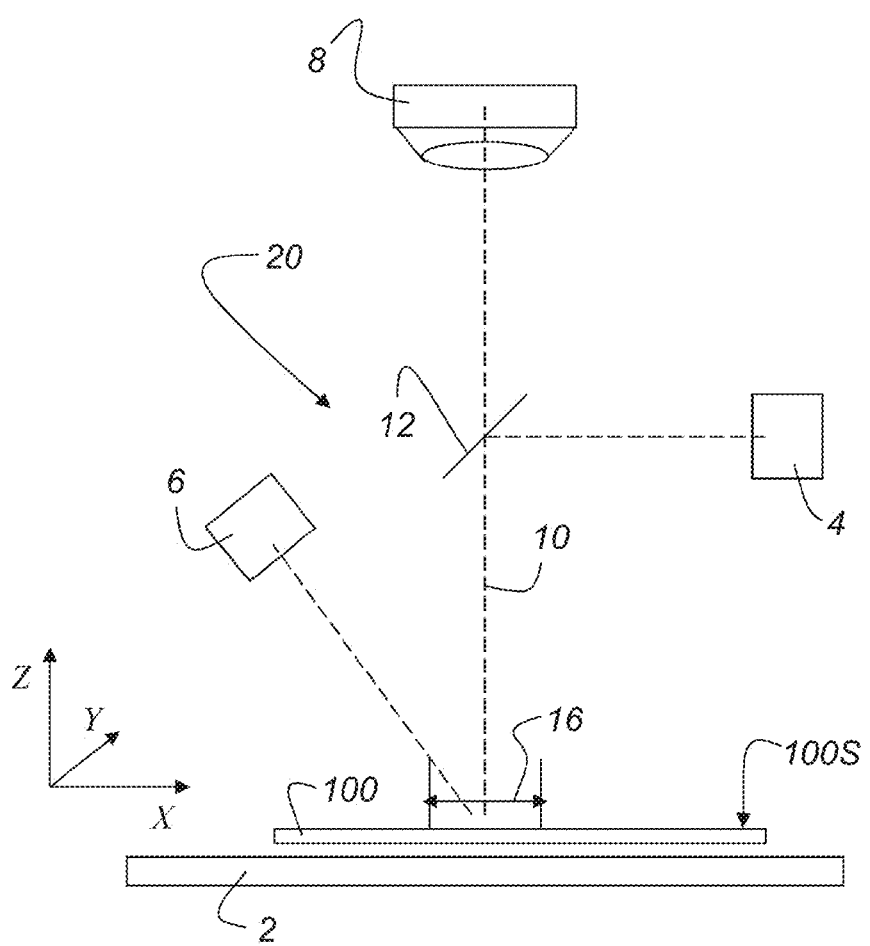
FIG. 2 shows a schematic optical setup for capturing an image of the surface of semiconductor devices, respectively disc-shaped objects or wafers.

FIG. 2 shows a schematic representation of an optical setup 20 of the inspection system 1 for recording an image of at least a portion of the surface 100S of a semiconductor device 100. A portion of a semiconductor device 100 may be an individual die 230. The semiconductor device 100 may be a wafer. The wafer is placed on a stage 2 movable in X-coordinate direction X and in Y-coordinate direction Y. For illuminating the surface 100S of the semiconductor device 100 at least one incident light illumination system 4 is provided. According to the embodiment shown in FIG. 2 the inspection system 1 is provided with at least incident light illumination system 4 and/or at least one dark-field illumination system 6. With the detector or a camera 8 the light from the surface 100S of the semiconductor device 100 can be converted to electric signals and used as image data for further analysis. In the embodiment shown here the light from the incident light illumination system 4 is coupled into a detection beam path 10 of the camera 8 by a beam splitter 12. The entire surface 100S of the semiconductor device 100 is recorded in a so-called meander scan. Therein always a strip 16 of the part of the surface 100S of the semiconductor device 100 is recorded. It is as well possible that the stage 2 moves to a X-position and a Y-position of an individual die 230 on the surface 100S of the semiconductor device 100. Individual dies 230 can be recorded and used for later re-inspection.

Figure 3:
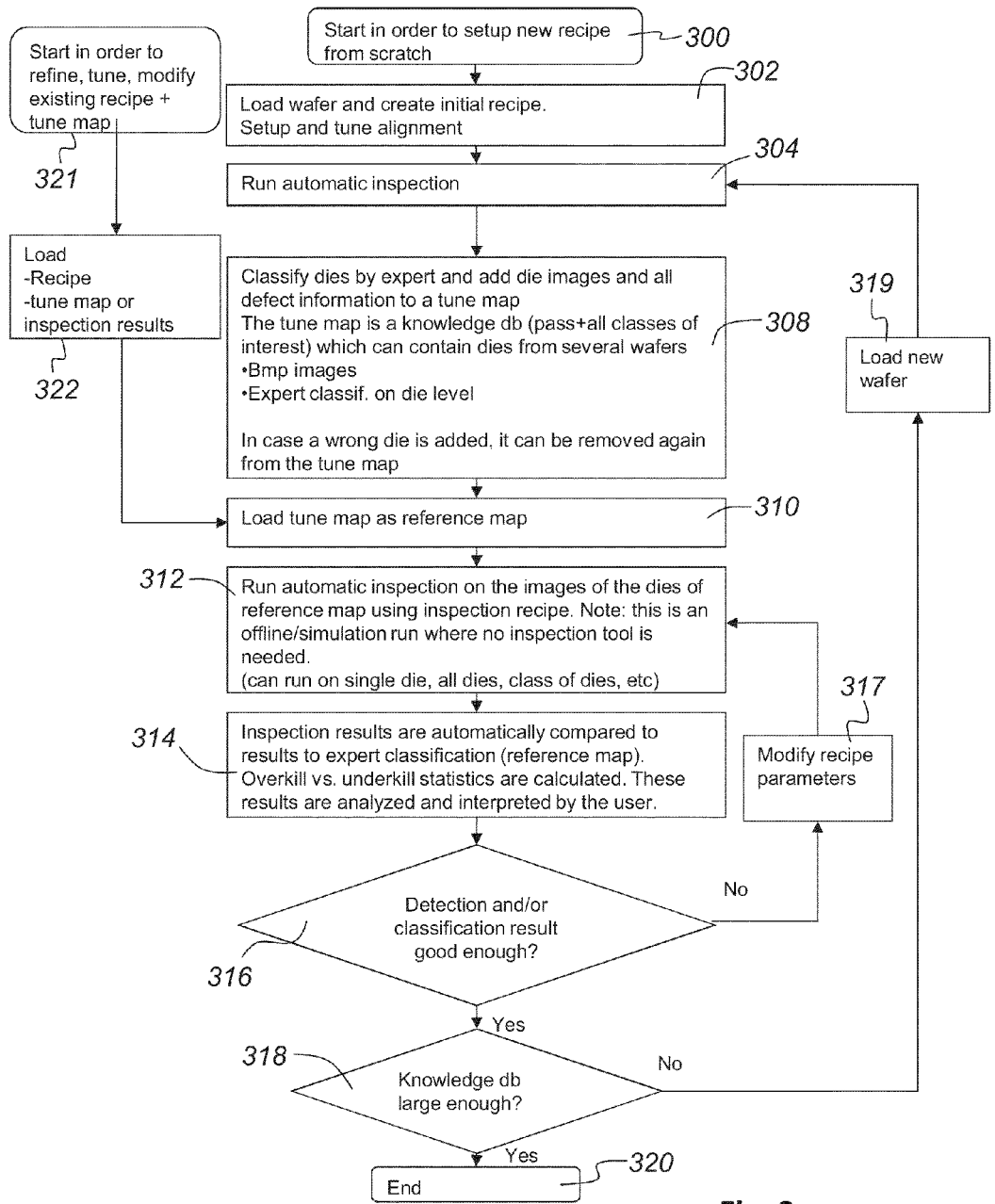
FIG. 3 shows a flow chart of the method for recipe generation for automated inspection of semiconductor devices.

FIG. 3 shows a flow chart of a method that allows for generation of a recipe for automated inspection from scratch and for refinement, tuning, and modification of existing recipes. The generation of a recipe from scratch is done when entry point 300 is used and the refinement, tuning, and modification of existing recipes is done when entry point 321 is used. Both versions of the method will be outlined in more detail in the paragraphs below. A key element of this method is the tune map 206T (see FIG. 7) which comprises inspection images of dies and related information which may include expert classifications and results of automated inspections. Once a tune map is available, the concept of the tune map allows to run automated inspections offline on the image data of the tune map that means without the need of an inspection system 1. After an automated inspection using inspection images of a tune map the inspections results can be compared to the expert classification and/or compared to inspection results of a previous inspection which was saved to the tune map. These comparisons of results may then be used to tune or modify recipe parameters in order to improve the inspection results that can be achieved with the recipe (minimize over and underkill). Inspection images and related information can be added to and removed from the tune map such that the tune map may comprise data from multiple wafers. Using die images of multiple wafers is important because certain defect types may only be present on some wafers while other defect types may only be present on other wafers. Furthermore, the tune map allows to add new defect types to an inspection recipe while ensuring that the performance of existing defect types does not deteriorate. If for example a new defect type N is added to an existing recipe that can already detect defect types K, L, M, then the new defect type may require the use of additional inspection methods/algorithms and/or parameters of already used inspection methods may have to be changed in order to detect the new defect type N. This may result in deterioration of inspection results on the already existing defect types K, L, M. With a tune map that comprises all defect types this deterioration of inspection results on the already existing defect types would be immediately visible such that it could be accounted for and underkill/overkill be minimized.

The flow chart of FIG. 3 shows an embodiment of the method for recipe generation for automated inspection of semiconductor devices 100 using an inspection system 1. The embodiment shown here describes the inspection recipe generation from scratch. At a start 300 there is no existing inspection recipe and no tune map (reference data set) for a specific type of wafer available. In a wafer loading and initial recipe step 302 a wafer 100 is loaded to an inspection system 1, an illumination is selected, an initial inspection recipe is generated, comprising wafer properties (e.g. die size, die pitch, etc.), and the wafer alignment step is setup and tuned. During the alignment step the x-y-axes of the wafer are detected and the wafer is rotated (usually by rotating the chuck) into a predefined orientation. Therefore at least a part of the wafer is scanned (inspection images are acquired) and features are defined in the alignment section of the inspection recipe such that the x-y-axes of the wafer can be automatically detected for any wafer of the same type when loaded to the system 1. The alignment may be done on wafer-level in case of un-diced wafers or on wafer-level and die-level in case of diced/sawn wafers. In the latter case features are found for a rough wafer-level alignment and features for fine image data based die-level alignment. The inspection parameters of the initial recipe are set to a predefined set of parameters or to any user selected values. Step 302 is followed by running automatic inspection 304 with the initial inspection recipe. With a classifying step 308 the dies are classified by an expert. The die images and all defect information are added to a tune map 206T (see FIG. 7). The tune map 206T is a knowledge database which contains pass dies and all dies from defect classes of interest. The tune map 206T can contain dies from several wafers 100. The image format of the die images can be bitmap such as bmp, tiff, gif and preferably lossless. In a further step 310 the existing tune map 206T (that was generated in step 308) is loaded as the reference wafermap 210. After the loading step 310 an automatic inspection step 312 on the images of the dies of the reference map 210 is carried out by using the inspection recipe. The automatic inspection step 312 can run on a single die, all dies, a class of dies etc. With an analyzing step 314 the inspection results are analyzed and interpreted. The inspection results are compared to the expert classification (reference map) of defects in dies. The inspection results comprise among others overkill and underkill information. Based on this information the user decides in a first decision step 316, if the detection and/or the classification result is good enough. If the decision is "Yes" the method proceeds to a second decision step 318. If the decision is "No" the method proceeds to a modifying step 317 of recipe parameters. The modified recipe parameters influence the automatic inspection step 312. In the second decision step 318 it is checked if the knowledge database is large enough. If the result of the check is "Yes" the method proceeds to an end 320. If the decision in the second decision step 318 is "No" the loading 319 of a new wafer 100 to the inspection system is carried out. The automatic inspection 304 of the new wafer is carried out in order to provide additional die images and defect/classification information in order to increase the tune map/knowledgebase.

The flow diagram of FIG. 3 shows as well an embodiment 321, wherein the user can refine, tune, and modify an existing inspection recipe for automated inspection of semiconductor devices given a tune map or an inspection result of a wafer is available. In case that an inspection result is loaded then this will be copied/loaded to a tune map. The recipe and the tune map are loaded in a loading step 322 which is followed by step 310 wherein the tune map that was loaded in loading step 322 is loaded as the reference map for the method for inspection recipe generation. The method for inspection recipe refining, tuning, modifying starts after the loading step 310 with the automatic inspection step 312 on the images of the dies of the loaded reference map 210 is carried out by using the loaded inspection recipe. The automatic inspection step 312 can run on a single die, all dies, a class of dies etc. With an analyzing step 314 the inspection results are analyzed and interpreted. The inspection results are compared to the expert classification. The inspection results comprise information on overkill and/or underkill that the user reviews in order to decide on inspection quality. In a first decision step 316 the decision is made, if the detection and/or the classification result is good enough. If the decision in 316 is "Yes" the method proceeds to a second decision step 318. If the decision in 316 is "No" the method proceeds to a modifying step 317 of recipe parameters. The modified recipe parameters influence the automatic inspection step 312. In the second decision step 318 the decision is made whether the knowledge data bases is large enough. If the decision in the second decision step 318 is "No" the loading 319 of a new wafer 100 to the inspection system is carried out. The automatic inspection 304 of the new wafer is carried out in order to provide additional die images and defect/classification information in order to increase the tune map/knowledgebase. If the result of the check in 318 is "Yes" the method proceeds to an end 320. Note that in the case where the decision in 318 is "Yes" the method works offline and does not need an inspection system 1.

Figure 4:
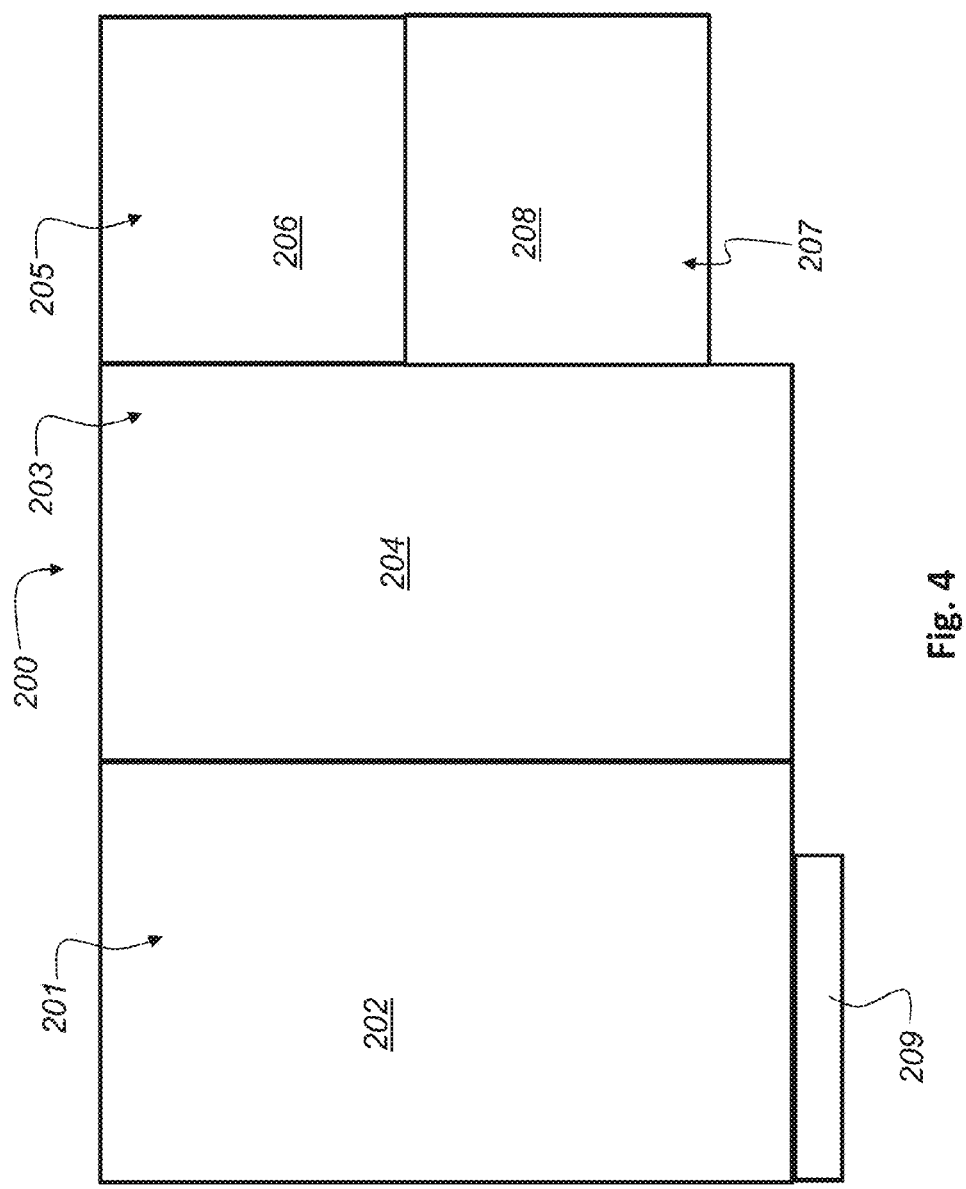
FIG. 4 shows a schematic representation of the dialog presented to a user on a user interface.

FIG. 4 shows a schematic representation of a dialog 200 presented to a user on a user interface 13 (see FIG. 1). The user interface is for example the user interface 13 of the inspection system 1 or it can be the user interface 13 of conventional workstation (not shown) with which the recipe tuning is carried out offline. In case the user works offline the relevant data for the recipe tuning are loaded to the workstation. The dialog 200 shows a reference section 202 of the tune pane (dialog 200), which is presented in a first window 201. A test section 204 of the tune pane (dialog 200), which is presented in a second window 203. A tune map section 206 of the tune pane (dialog 200), which is presented in a third window 205. A classification table section 208 of the tune pane (dialog 200), which is presented in a fourth window 207. The tune pane (dialog 200) can be used for the entire tuning process.

Figure 5:
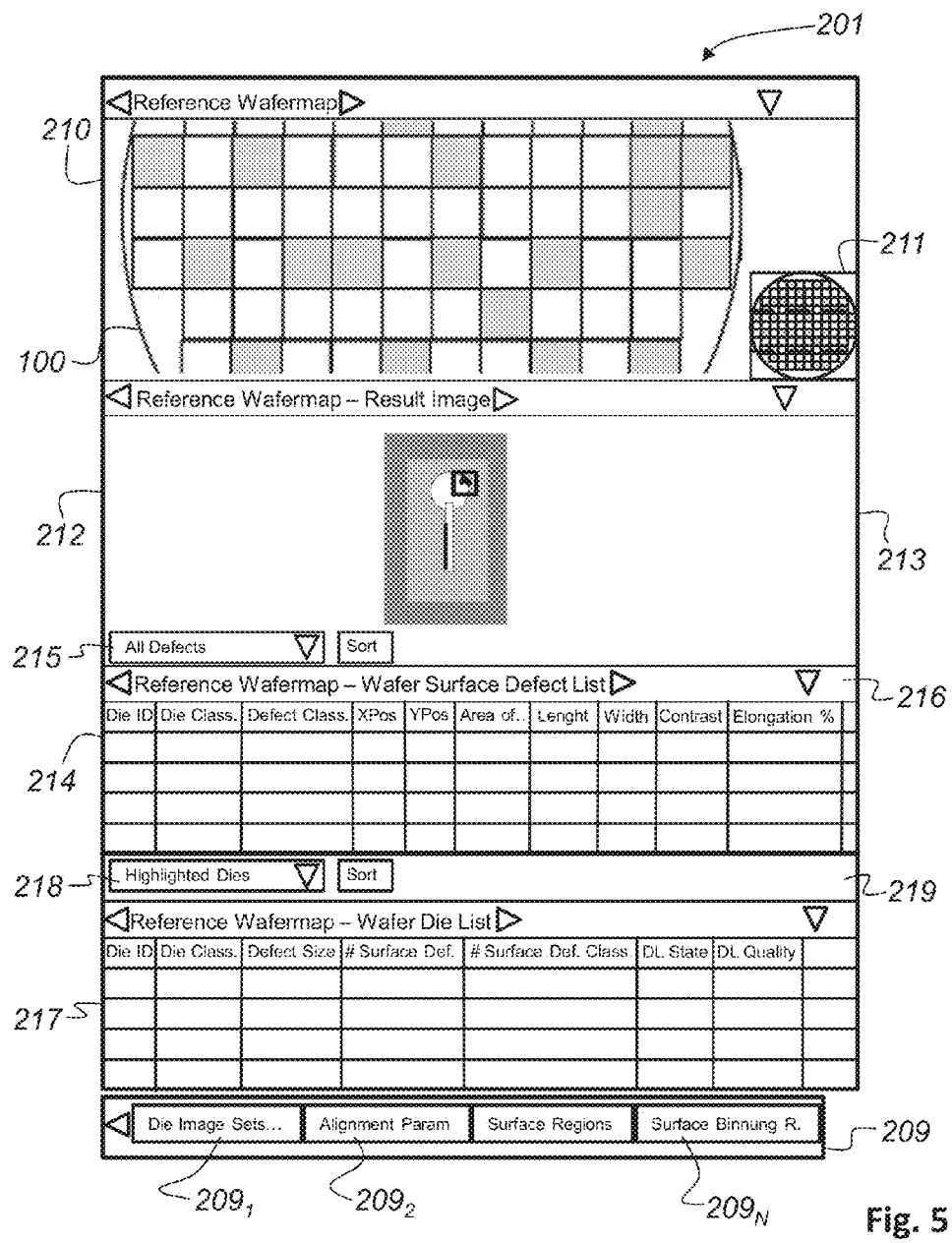
FIG. 5 shows a first window of the user interface which is the reference section of the tune pane.

FIG. 5 shows an embodiment of the first window 201 presented on the user interface 13. The first window 201 is the reference section 202 of the dialog 200 (tune pane). The reference section 202 shows a reference wafermap 210 and a small image 211 of the whole wafer 100, so that the user gets an indication which part of the surface of the wafer 100 is displayed with the reference wafermap 210. The reference wafermap 210 can be obtained by various ways. One possibility is that a reference wafermap 210 is loaded from a storage device (no shown) where previous reference wafermaps 210 of the same wafer type or different wafer types are stored. It is possible to load a tune map 260T. A reference wafermap 210 can be generated by running a wafer 100 on an inspection system 1. The wafer 100 can be a wafer from one lot which needs to be inspected during the production process. As mentioned before the size of the knowledgebase determine the amount of wafers to be loaded to the inspection system 1

The first window 201 shows as well at least one result image 212 of the reference wafermap 210. A small image 213 of the result image 212 is displayed in the result image 212 of the reference wafermap 210, so that the user received information about the position within the displayed result image 212.

The first window 201 shows below the result image 212 a wafer surface defect list 214 of the reference wafermap 210. The wafer surface defect list 214 provides information about the defect found in the reference wafermap 210. The information shown consists of the "die ID", the "die classification", the "X-position" of the die with the defect on the surface of the wafer 100, the "Y-position" of the die with the defect on the surface of the wafer 100, the "area" of the defect, the "length" of the defect, the "width" of the defect; the "contrast" of the defect and the "elongation" of the defect. It is absolutely clear for a skilled person that information of the defect presented here is not a closed list. A selection bar 215 allows the user to select a specific defect type and to sort the wafer surface defect list 214 according to the selected defect type. A scroll bar 216 enables the user to navigate within the wafer surface defect list 214.

The first window 201 shows below wafer surface defect list 214 a wafer die list 217 of the reference wafermap 210. The wafer die list 217 provides information about the defect found in the reference wafermap 210. The information shown consists of the "die ID", the "die classification", the "defect size" of the die with the defect on the surface of the wafer 100, the "number of surface defects", the "number of the surface defect classification", the "width" of the defect and the "elongation" of the defect. It is absolutely clear for a skilled person that information of the defect presented here is not a closed list. A selection bar 218 allows the user to select a specific dies and to sort the wafer die list 217 according to the selected dies. A scroll bar 219 enables the user to navigate within the wafer die list 217. Below the first window 201 a shortcut section 209 of the dialog 200 is displayed. The shortcut section 209 allows direct access to recipe editing panes like: "die image sets . . . ", "alignment parameters", surface regions" or "classification parameters". There is no need to save it prior to a test run. The shortcut section 209 is a toolbar which can be configured by the user. The toolbar shows a plurality of various buttons $209_1$, $209_2$, . . . , $209_N$ which provide the links to the shortcuts. When clicking on one of the buttons $209_1$, $209_2$, . . . , $209_N$ of the shortcuts, the related parameters will be shown.

Figure 6:
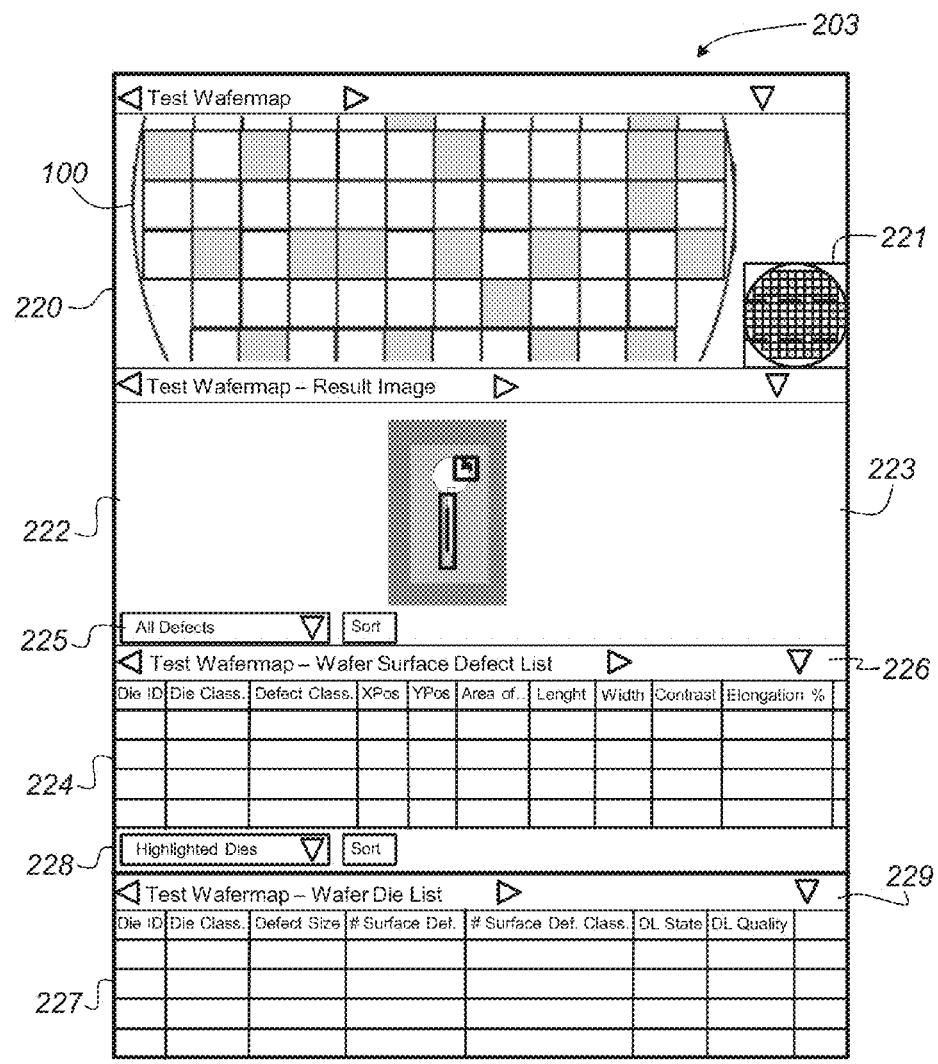
FIG. 6 shows a second window of the user interface which is the test section of the tune pane.

FIG. 6 shows a second window 203 of the user interface 13 which is the test section 204 of the tune pane (dialog 200). The test section 204 shows a test wafermap 220 and a small image 221 of the whole wafer 100, so that the user gets an indication which part of the surface of the wafer 100 is displayed with the test wafermap 220. The test wafermap 220 shows the result of the latest run carried out with the reference wafermap 210. The second window 203 shows as well at least one result image 222 of the test wafermap 220. A small image 223 of the result image 222 is displayed in the result image 222 of the test wafermap 220, so that the user receives information about the position within the displayed result image 222. The second window 203 shows below the result image 222 of the test wafermap 220 a wafer surface defect list 224 of the test wafermap 220. The wafer surface defect list 224 provides information about the defect found in the test wafermap 220. The information shown consists of the "die ID", the "die classification", the "defect classification" the "X-position" of the die with the defect on the surface of the wafer of the test wafermap 220, the "Y-position" of the die with the defect on the surface of the wafer of the test wafermap 220, the "area" of the defect, the "length" of the defect, the "width" of the defect; the "contrast" of the defect and the "elongation" of the defect. It is absolutely clear for a skilled person that information of the defect presented here is not a closed list. A selection bar 225 allows the user to select a specific defect type and to sort the wafer surface defect list 224 according to the selected defect type. A scroll bar 226 enables the user to navigate within the wafer surface defect list 224. The second window 203 shows below wafer surface defect list 224 of the test wafermap 222 a wafer die list 227 of the test wafermap 220. The wafer die list 227 provides information about the defect found in the test wafermap 220. The information shown consists of the "die ID", the "die classification", the "defect size" of the die with the defect on the surface of the wafer 100, the "number of surface defects", the "number of the surface defect classification", the "width" of the defect and the "elongation" of the defect. It is absolutely clear for a skilled person that information of the defect presented here is not a closed list. A selection bar 228 allows the user to select specific dies and to sort the wafer die list 227 according to the selected dies. A scroll bar 229 enables the user to navigate within the wafer die list 227.

Figures 7, 8:
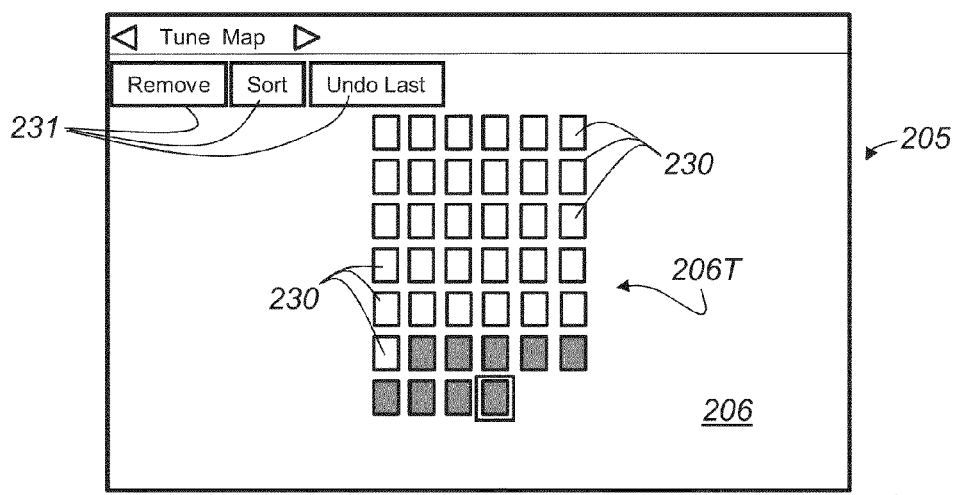
FIG. 7 shows a third window of the user interface which is the tune map section of the tune pane.
FIG. 8 shows a forth window of the user interface which is the classification table of the tune pane.

FIG. 7 shows a third window 205 of the user interface 13 which is the tune map section 206T of the tune pane (dialog 200). The tune map 206T contains dies of interest 230. Dies 230 from multiple wafers 100 can be added by the user to the tune map 206T. Additionally, the die classification can be chosen by the user. The different classification is shown with different shadings of the individual dies 230. The user can select several buttons 231, with which influence the dies of interest 230 shown in the tune map 206T. The possible actions are written on the buttons 231.

FIG. 8 shows a forth window 207 of the user interface 13 is the classification table 208 of the tune pane (dialog 200). The classification table 208 shows the comparison results between the reference wafermap 210 and the test wafermap 220. The classification table 208 is used as a selection input, wherein for example highlighted dies will be inspected. Moreover the classification table 208 allows easy tracking of underkill or overkill and the differences between different runs are easy to monitor.

The invention has been described with reference to specific embodiments. It is obvious to a person skilled in the art, however, that alterations and modifications can be made without leaving the scope of the subsequent claims.

LIST OF REFERENCE NUMERALS 1 inspection system
2 stage
3 cartridge element
4 incident light illumination system
5 inspection unit
6 dark-field illumination system
8 camera
9 transport device
10 detection beam path
11 housing
12 beam splitter
13 interface, dialog, tune pane
14 keyboard
15 computer system
100 semiconductor device, wafer
100S surface semiconductor device
200 dialog/tune pane
201 first window 202 reference section
203 second window
204 test section
205 third window
206 tune map section,
206T tune map
207 classification table section
208 fourth window
209 shortcut section
$209_1, 209_2, \ldots, 209_N$ various buttons
210 reference wafermap
211 small image
212 result image
213 small image of result image
214 wafer surface defect list
215 selection bar
216 scroll bar
217 wafer die list
218 selection bar
219 scroll bar
220 test wafermap
222 result image
223 small image of result image
224 wafer surface defect list
225 selection bar
226 scroll bar
227 wafer die list
228 selection bar
229 scroll bar
230 dies of interest
231 several buttons
300 start
302 loading step
304 automatic inspection
308 classifying step
310 loading step
312 inspection step
314 analyzing step
316 first decision step
317 modifying step
318 second decision step
319 loading
320 end
321 refining and/or tuning and/or modifying step
322 loading step
X X-coordinate direction
Y Y-coordinate direction
Z Z-coordinate direction

What is claimed is:

1. A method for inspection recipe generation for automated inspection of semiconductor devices, comprising at least one of the following groups of steps based on an initial condition:
when creating an initial recipe:
using a reference data set for inspection recipe generation;
running automatic inspection with the initial recipe on captured images of dies of the reference data set with an inspection system;
classifying the detected inspection results from the automatic inspection and comparing the classified inspection results with an expert classification of defects in dies;
generating overkill and underkill numbers; and
modifying inspection recipe parameters and repeating the automatic inspection if the detection and/or the classification of a test data set is below a predefined threshold using saved images of dies to iteratively improve the inspection recipe parameters for use in future semiconductor device production; or,
when starting with the initial inspection recipe and a knowledge database of dies is not large enough:
using a reference data set for inspection recipe generation;
running automatic inspection with the initial recipe to capture images of dies of a new semiconductor device loaded into the inspection system;
classifying the detected inspection results from the automatic inspection and comparing the classified inspection results with the expert classification of defects in dies;
generating overkill and underkill numbers; and
modifying inspection recipe parameters and repeating the automatic inspection if the detection and/or the classification of the test data set is below the predefined threshold using saved images of dies to iteratively improve the inspection recipe parameters for use in future semiconductor device production.

2. The method of claim 1, wherein the reference data set is a stored reference map or a tune map which is uploaded to a computer.

3. The method of claim 2, wherein a refining, tuning and modifying of the existing reference map or the existing tune map is carried out prior to the upload to the computer.

4. The method of claim 1, wherein the existing inspection recipe is stored and is uploaded to a computer.

5. The method of claim 4, wherein a refining, tuning and modifying of the existing initial inspection recipe is carried out prior to the upload to the computer.

6. The method of claim 1, wherein the tune map contains dies of interest and a die classification is selectable by the user.

7. The method of claim 6, wherein dies from different semiconductor devices are assed to the tune map.

8. The method of claim 1 wherein a classification table shows comparison results between the reference data set and the test data set, wherein the test data set is a test map.

9. The method of claim 1, wherein prior to using the reference data set for inspection recipe generation, the generation of the data set and of the initial recipe comprise the steps of:
loading a semiconductor device into an inspection system;
performing a setup and a tune alignment;
inspecting the semiconductor device with the inspection system;
classifying dies on the semiconductor devices; and
adding die images and defect information to a tune map.

10. The method of claim 9, wherein a new semiconductor device is loaded into the inspection system if a knowledge database of dies of the tune map is not large enough and automatic inspection of the newly loaded semiconductor device is carried out.

11. A computer system for inspection recipe generation for automated inspection of semiconductor devices comprising:
an inspection system arranged to capture images of dies on one or more wafers;
a computer arranged to use a reference data set for inspection recipe generation and run an automatic inspection with an initial recipe on the images of dies of the reference data set;
a dialog, with a first window showing at least the reference data, a second window showing at least test data; a third window showing a tune map and a fourth window showing a classification table which enables a comparison between the classified inspection results and an expert classification of defects in dies, with regard to the overkill and underkill numbers, wherein the computer is arranged to perform a generation and display of overkill and underkill numbers, and to modify inspection recipe parameters and repeat the automatic inspection if the detection and/or the classification of a test data set is below a predefined threshold using saved images of dies to iteratively improve the inspection recipe parameters for use in future semiconductor device production.

12. The computer system of claim 11, wherein the reference data set is a stored reference map or a tune map which is uploaded to the computer.

13. The computer system of claim 12, wherein a refining, tuning and modifying of the existing reference map or the existing tune map is carried out prior to the upload to the computer.

14. The computer system of claim 11, wherein the existing inspection recipe is stored and is uploaded to the computer system.

15. The computer system of claim 14, wherein a refining, tuning and modifying of the existing initial inspection recipe is carried out prior to the upload to the computer.

16. The computer system of claim 11, wherein tune map contains dies of interest and a die classification is selectable by the user via the dialog.

17. The computer system of claim 16 wherein dies from different semiconductor devices are assed to the tune map and displayed in the third window of the dialog.

18. The computer system of claim 11, wherein a classification table of the fourth shows comparison results between the reference data set and a test data set, wherein the test data set is the test map.

19. The computer system of claim 11, wherein the inspection system is connected to the computer system and the inspection system is used to run automatic inspection of a loaded semiconductor device.

20. The computer system for inspection recipe generation for automated inspection of semiconductor devices of claim 11, wherein a new semiconductor device is loaded into the inspection system if a knowledge database of dies is not large enough and automatic inspection of the newly loaded semiconductor device is carried out and the new images are added to the knowledge database.

21. An apparatus for inspection recipe generation for automated inspection of semiconductor devices comprising:
an inspection system, comprising:
an incident light illumination system;
a camera arranged to receive light from a surface of the semiconductor devices, wherein the light is converted to electric image data for further analysis;
a computer arranged to use a reference data set for inspection recipe generation and run an automatic inspection with an initial recipe on images of dies of the reference data set, in order to modify inspection recipe parameters by iteratively improving the inspection recipe parameters of a test data set using saved images of dies for use in future semiconductor device production; and
at least one display, which is subdivided into a first window, a second window, a third window and a fourth window; wherein the first window showing at least the reference data, the second window showing at least test data; the third window showing a tune map and the fourth window showing a classification table which enables a comparison between images of the classified inspection results and images of an expert classification of defects, with regard to the overkill and underkill numbers which are generated and displayed.

22. The apparatus of claim 21, wherein an input device enables a modification of the inspection recipe parameters and repeating the automatic inspection if the detection and/or the classification is below a predefined threshold.

23. The apparatus of claim 22, wherein the reference data set is a stored reference map or a tune map which is uploaded to the computer; a refining, tuning and modifying of the reference map or the tune map is carried out prior to the upload to the computer.

24. The apparatus of claim 21, wherein the existing inspection recipe is stored and is uploaded to the computer, wherein a refining, tuning and modifying of the existing initial inspection recipe is carried out prior to the upload to the computer.

25. The apparatus for inspection recipe generation for automated inspection of semiconductor devices of claim 21, wherein a new semiconductor device is loaded into the inspection system if a knowledge database of dies is not large enough and automatic inspection of the newly loaded semiconductor device is carried out and the new images are added to the knowledge database.

* * * * *